US006991636B2

(12) United States Patent
Rose (10) Patent No.: US 6,991,636 B2
(45) Date of Patent: Jan. 31, 2006

(54) NITINOL LOOP SUTURE PASSER (75) Inventor: Donald J. Rose, New York, NY (US)

(73) Assignee: Arthrex, Inc., Naples, FL (US)

( * ) Notice: Subject to any disclaimer, the term of this patent is extended or adjusted under 35 U.S.C. 154(b) by 10 days.

(21) Appl. No.: 10/646,827

(22) Filed: Aug. 25, 2003

(65) Prior Publication Data
US 2004/0097975 A1 May 20, 2004

Related U.S. Application Data (60) Provisional application No. 60/405,710, filed on Aug. 26, 2002.

(51) Int. Cl.
A61B 17/04 (2006.01)
(52) U.S. Cl. ...................... 606/148; 606/139
(58) Field of Classification Search ............... 606/139, 606/144, 148, 146, 187, 232; 289/2.5, 17; 223/104
See application file for complete search history.

(56) References Cited

U.S. PATENT DOCUMENTS

| 4,441,497 A | * | 4/1984 | Paudler | 606/225 |
| 5,403,331 A | * | 4/1995 | Chesterfield et al. | 606/148 |
| 5,562,683 A | * | 10/1996 | Chan | 606/139 |
| 5,562,684 A | * | 10/1996 | Kammerer | 606/139 |
| 5,681,333 A | * | 10/1997 | Burkhart et al. | 606/148 |
| 5,697,950 A | * | 12/1997 | Fucci et al. | 606/232 |
| 5,746,752 A | * | 5/1998 | Burkhart | 606/139 |
| 5,746,754 A | * | 5/1998 | Chan | 606/148 |
| 5,755,728 A | * | 5/1998 | Maki | 606/145 |
| 5,776,151 A | * | 7/1998 | Chan | 606/148 |
| 5,800,447 A | * | 9/1998 | Wenstrom, Jr. | 606/139 |
| 5,906,624 A | * | 5/1999 | Wenstrom, Jr. | 606/139 |
| 6,045,574 A | * | 4/2000 | Thal | 606/232 |
| 6,368,335 B1 | * | 4/2002 | Chan | 606/146 |
| 6,629,984 B1 | * | 10/2003 | Chan | 606/148 |
| 2001/0016747 A1 | * | 8/2001 | Romano et al. | 606/148 |

* cited by examiner

Primary Examiner—Glenn K. Dawson
Assistant Examiner—Michael G. Mendoza
(74) Attorney, Agent, or Firm—Dickstein Shapiro Morin & Oshinsky, LLP

(57) ABSTRACT

A suture shuttle in the form of a loop of flexible metallic material, such as nitinol wire, is disclosed. The flattened loop of nitinol wire is long enough to extend into an arthroscopic portal and out an accessory portal through a joint undergoing arthroscopic surgery. After installing a suture anchor in bone, a strand of suture attached to the suture anchor is retrieved through the accessory portal. Using a cannulated instrument having a sharp tip, the tissue to be repaired is pierced to create an opening. The nitinol loop is deployed through the cannulated instrument and passed through the opening. The retrieved suture strand is placed through the portion of the nitinol loop and pulled through the tissue opening before arthroscopic knots are tied.

5 Claims, 14 Drawing Sheets

NITINOL LOOP SUTURE PASSER

This application claims the benefit of U.S. Provisional Application No. 60/405,710, filed Aug. 26, 2002.

BACKGROUND OF THE INVENTION

1. Field of the Invention

The present invention relates to suture fixation, and more particularly, to a method and apparatus for using a looped nitinol wire suture passer for arthroscopic suture fixation of tissue.

2. Description of the Related Art

Arthroscopic suturing techniques and instruments have been developed in order to facilitate the suturing of tissue during arthroscopic surgical procedures. In arthroscopic surgery, access to a surgical work site within a patient's body is normally provided through one or more portals formed directly in the patient's body or through one or more cannulas inserted into the patient's body through small incisions. A chosen surgical procedure is carried out by a surgeon through the use of elongated instruments inserted through these cannulas and it often becomes necessary to suture selected tissue at the surgical work site.

Since the work site is only accessible through a small portal or cannula and since it is very difficult to tie sutures within the body, various devices and techniques have been developed to enable the surgeon to manipulate sutures arthroscopically. For example, some procedures enable the surgeon to pass suture material through selected tissue, form a surgical knot extracorporeally and then move the knot with a knot pusher through the portal or cannula into position adjacent the desired tissue to be sutured. Some instruments used to pass the suture incorporate a hollow needle provided with some means, often a wire loop, to guide suture through the tissue pierced by the needle. See, e.g., U.S. Pat. No. 5,755,728, which discloses a non-metallic suture shuttle having loops on opposite ends for passing through the bore of a roller type suture passing device. In one embodiment, each loop of the suture shuttle includes a short leader portion in the form of a single strand monofilament for threading the suture shuttle through the bore of the elongated instrument. In another embodiment, the short leader portion is eliminated, and the surgeon must squeeze the leading loop together to insert the shuttle into the bore of the elongated instrument.

It would be desirable to provide a suture shuttle for insertion in bore of an elongated which does not require either a monofilament leader portion or the step of squeezing the leading loop.

SUMMARY OF THE INVENTION

In accordance with the present invention, a length of suture is passed through tissue arthroscopically using a suture shuttle in the form of a loop of flexible metallic material, such as nitinol wire.

The loop of nitinol wire is formed by crimping a length of nitinol wire to form an acute bend in the middle of its length. The two ends of the wire opposite the bend are held together by a small shrink sleeve, for example, to form a flattened nitinol loop. The nitinol loop is long enough to extend into a portal and out an accessory portal through a joint undergoing surgery, as explained further below.

The procedure begins in a preferred embodiment of the invention by installing a suture anchor in bone in a joint to be repaired. One strand of suture attached to the suture anchor is retrieved and brought outside the body through an accessory portal. Using a cannulated passer instrument having a sharp tip, the tissue to be attached to the bone is pierced to create an opening. The nitinol loop is deployed through the cannulated passer, advanced through the opening in the tissue, and is retrieved and brought out through the accessory portal. While holding the nitinol loop, the cannulated instrument is removed, leaving the nitinol loop in place.

The suture strand that was retrieved through the accessory portal is placed through the portion of the nitinol loop extending from the accessory portal. Pulling on the opposite end of the nitinol loop delivers the suture back through the opening in the tissue. Arthroscopic knots are then tied in the normal fashion to secure the tissue to the suture anchor.

The preferred metallic material for the flexible loop is an alloy of nickel and titanium known in the art as nitinol (NiTi), a shape memory alloy. Although other materials could be used, such as stainless steel or monofilament polymers, shape memory alloys, and nitinol in particular, are preferred. The material and the loop closure have to be strong enough to be able to pull through the joint. The loop can be an open loop (open at the back end) or a closed loop. A closed loop can be used in both an antegrade and a retrograde fashion. The radius on the front end of the loop is critical, and the use of nitinol allows for a strong strand with a very small radius that will pass through a small diameter, acutely curved tip of a cannulated passer. The nitinol wire can be formed of three stranded braided nitinol. The wire must be crimped down on itself to offset the tendency of the wire to spread out when pushed through the joint. Such crimping to a small diameter radius would not be possible with a plastic material, as proposed in the above-mentioned U.S. Pat. No. 5,755,728.

The cannulated passer of the present invention is provided in various configurations, including left and right curves, which are useful in various types of arthroscopic surgery, particularly shoulder applications. The apparatus and method of the present invention also can be used in tissue plication, for example, to address capsule laxity of the shoulder.

DETAILED DESCRIPTION OF THE PREFERRED EMBODIMENT

Figure 1:
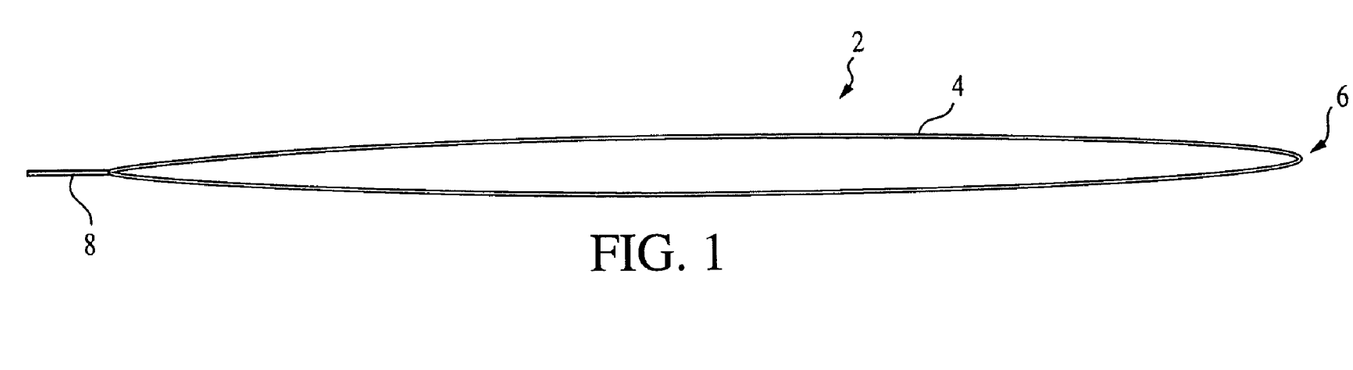
FIG. 1 illustrates a nitinol wire loop according to an exemplary embodiment of the present invention.

Referring now to the drawings, where like elements are designated by like reference numerals, FIG. 1 shows a suture shuttle in the form of a nitinol loop 2 formed from a length of nitinol wire 4, preferably three-stranded braided nitinol. Nitinol wire 4 is folded over on itself, and a radius 6 is formed at the fold. The radius is formed by drawing the wire through a bushing having a narrow opening. The wire preferably is able to withstand a 5 lb. pull at the radius area with the force being applied at approximately 90° from the bend.

Nitinol wire 4 can be provided in an open or closed loop. In the preferred embodiment of the invention, wire 4 is provided in a closed loop with the ends of the wire opposite the fold being held together with a short length of shrink sleeve tubing 8. The use of shrink tubing secures the ends without adding significantly to the overall axial diameter of the nitinol wire loop construct. Nitinol loop 2 preferably is about 22" long, sufficient to extend into a portal and out an accessory portal through a joint undergoing surgery, as explained further below.

Figure 2:
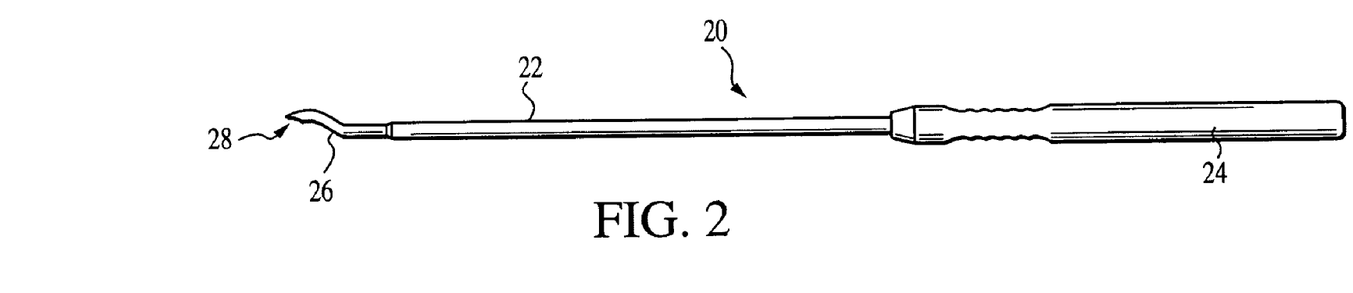
FIG. 2 is an elevation view of a cannulated passer according to the present invention.
Figure 3:
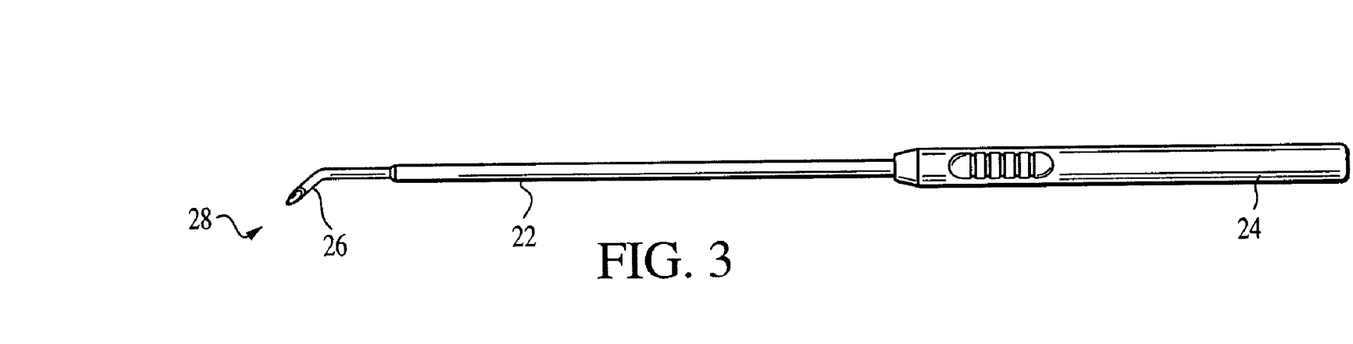
FIG. 3 is a plane view of a cannulated passer according to the present invention.

Referring to FIGS. 2 and 3, a cannulated passer 20 for nitinol loop 2 is shown. Passer 20 includes a cannulated shaft made of stainless steel, for example, secured to a cannulated handle 24. Cannulated shaft 22 tapers to a helically shaped end portion 26 provided with a sharp tip 28.

Figure 4:
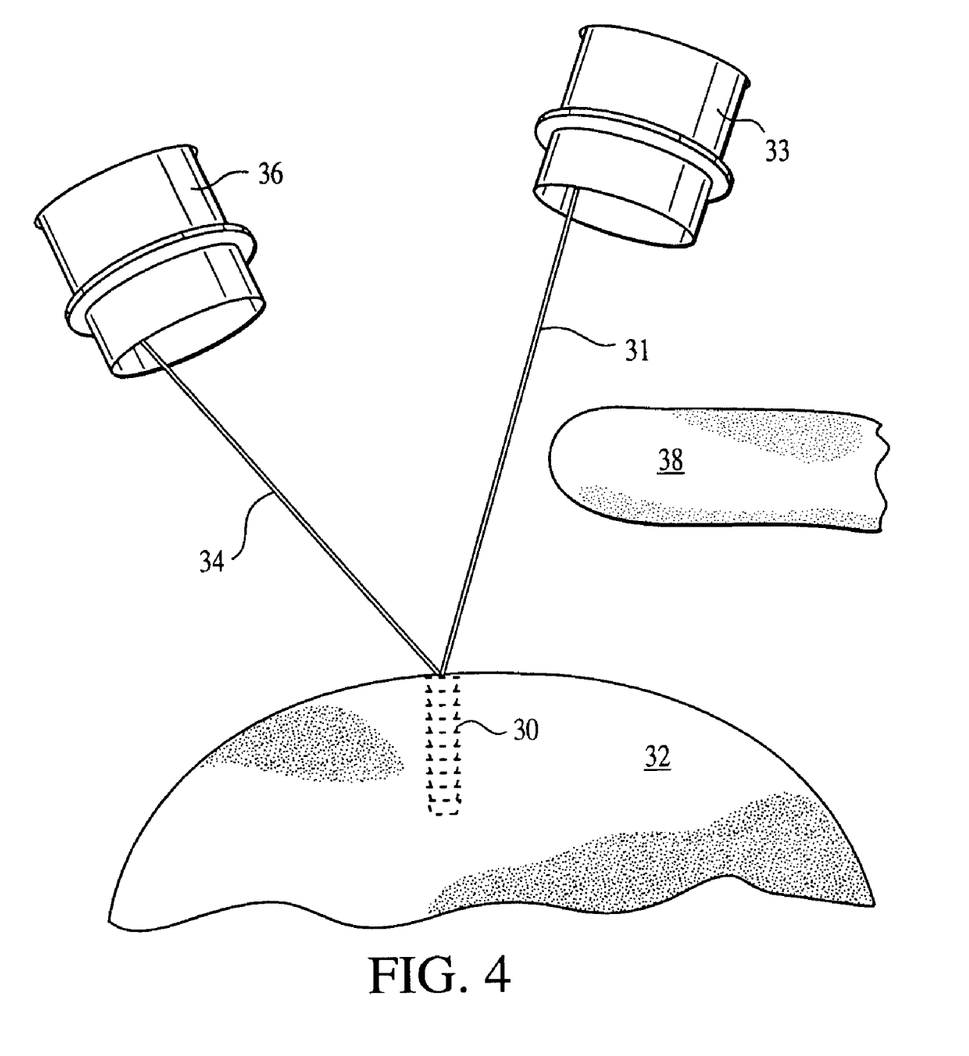
FIG. 4 illustrates an initial step in a shoulder repair procedure according to the present invention, in which one end of a suture attached to a suture anchor is retrieved through one portal and another end is retrieved through an accessory portal.
Figure 5:
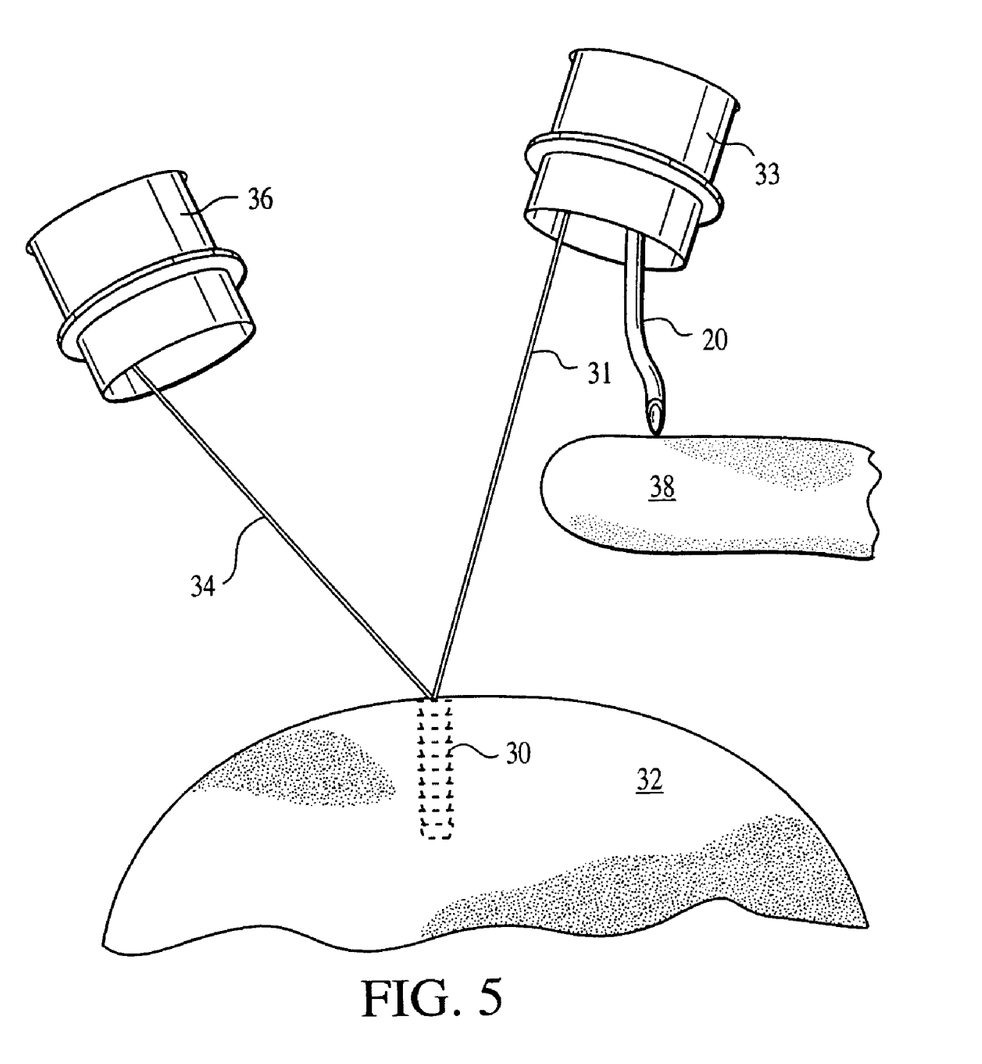
FIG. 5 illustrates a step subsequent to the step shown in FIG. 4, in which a passer instrument is deployed through the first portal up to the tissue to be sutured.
Figure 6:
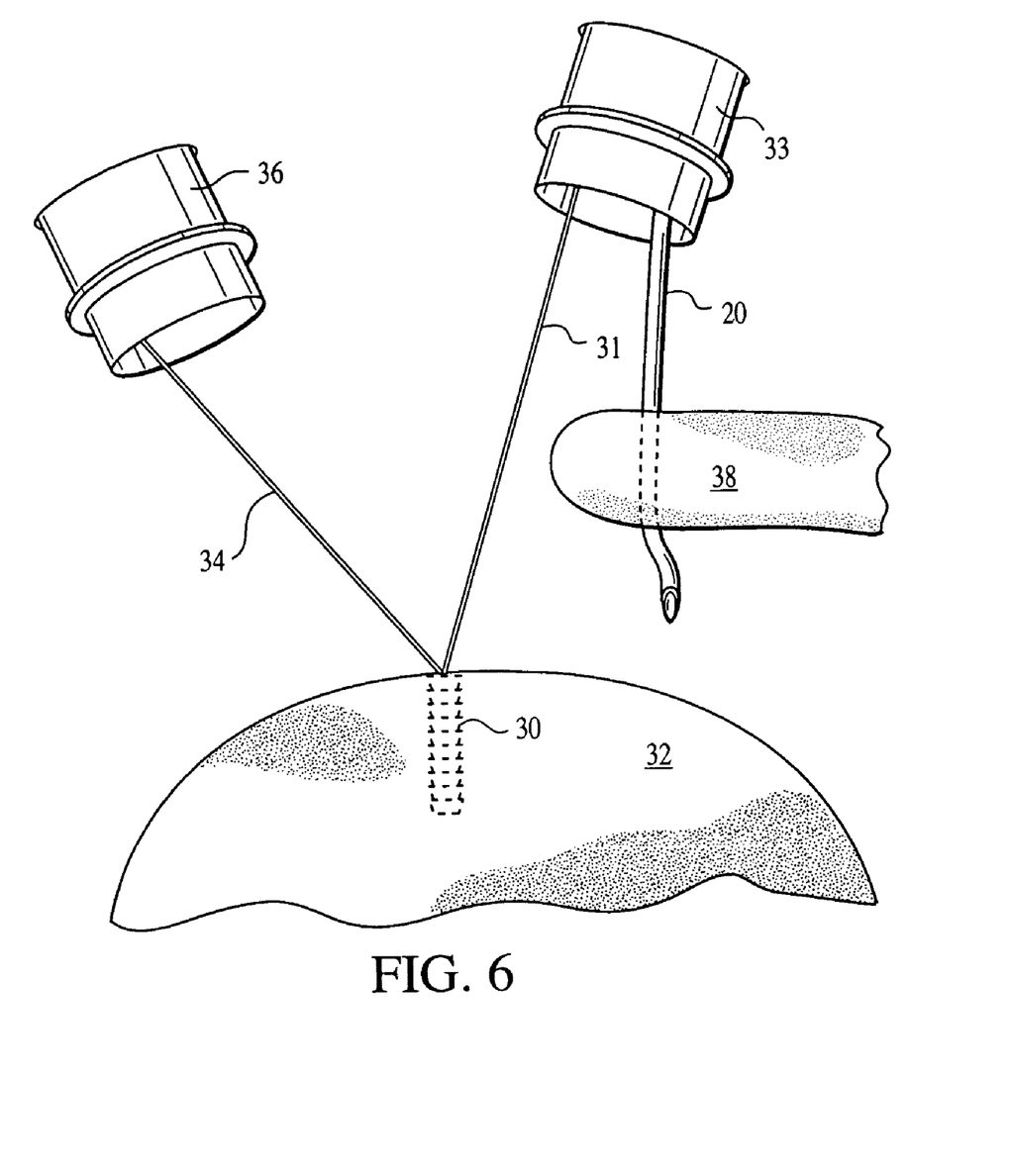
FIG. 6 illustrates a step subsequent to the step shown in FIG. 5, in which the passer instrument pierces through the tissue to be sutured.
Figure 7:
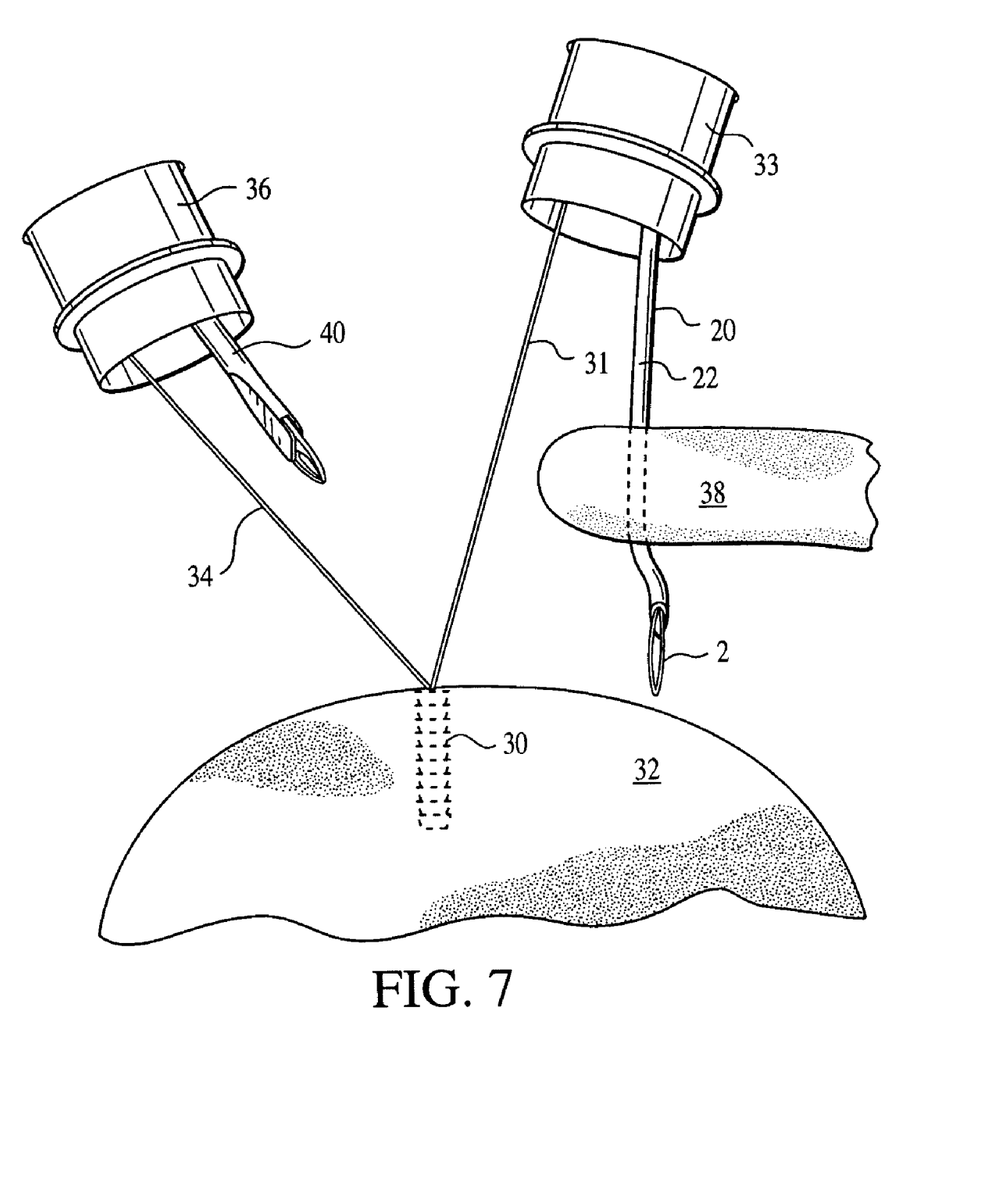
FIG. 7 illustrates a step subsequent to the step shown in FIG. 6, in which the nitinol loop is deployed through the shaft of the passer and a retrieving instrument is deployed through the accessory portal.
Figure 8:
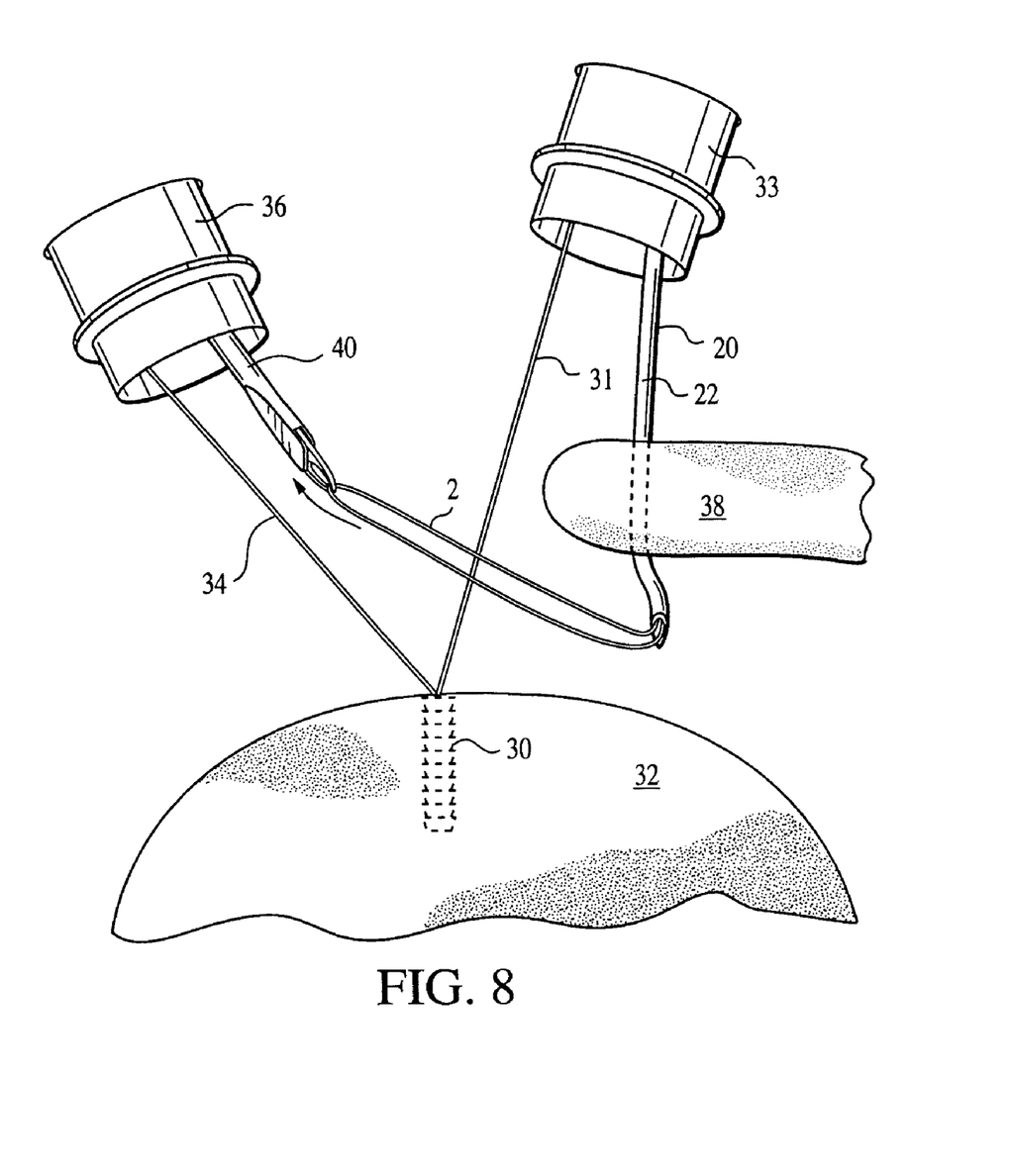
FIG. 8 illustrates a step subsequent to the step shown in FIG. 7, in which the nitinol loop is captured by the retrieving instrument.
Figure 9:
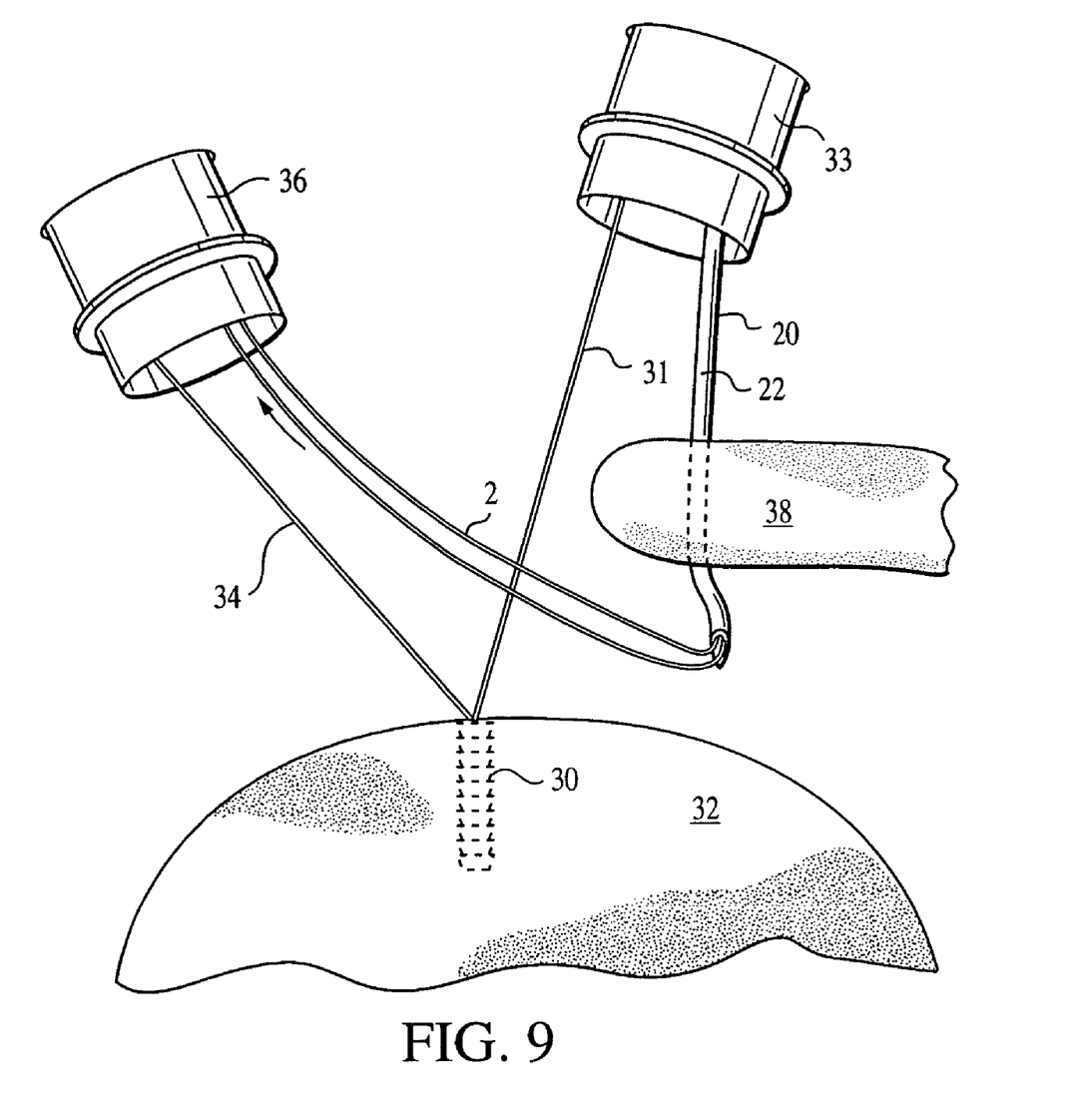
FIG. 9 illustrates a step subsequent to the step shown in FIG. 8, in which the retrieving instrument, carrying the nitinol loop, is retracted through the accessory portal.

A method of securing tissue according to the present invention is illustrated in FIGS. 4–17. The present invention may be used in a number of surgical procedures involved arthroscopic tissue tying, such as rotator cuff repair or shoulder instability repair. Referring first to FIG. 4, the procedure as applied to repairing shoulder instability begins by installing a suture anchor 30 in bone 32, at a point where capsular tissue 38 is desired to be fixed. One strand 31 of suture attached to suture anchor 30 is retrieved and brought outside the body through portal 33 and the other strand 34 is retrieved and brought outside the body through an accessory portal 36. As shown in FIG. 5, passer 20 is deployed from portal 33 toward capsular tissue 38 to be fixed, and then driven through capsular tissue 38 to create an opening through the tissue, as shown in FIG. 6. Next, referring to FIG. 7, nitinol loop 2 is deployed through shaft 22 of passer 20, and forceps 40 is deployed through accessory portal 36. Next, forceps 40 and passer 20 are maneuvered, and nitinol loop 2 is deployed as necessary for nitinol loop 2 to be secured in forceps 40, as shown in FIG. 8. As shown in FIG. 9, forceps 40 and nitinol loop 2 are retracted into and through accessory port 36.

Figure 10:
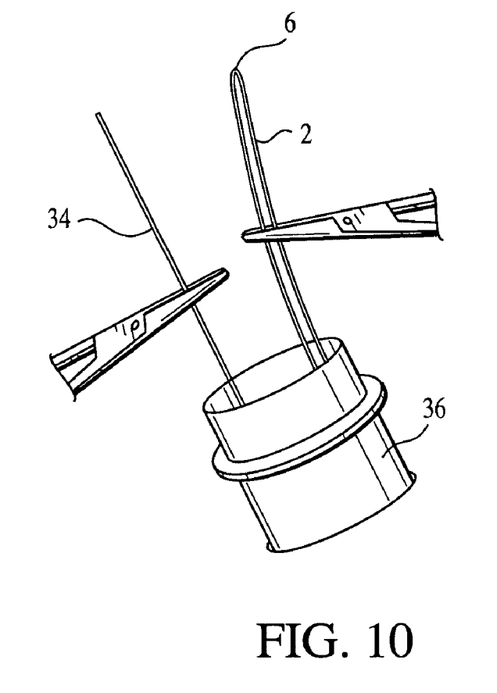
FIG. 10 illustrates a step subsequent to the step shown in FIG. 9, in which the nitinol loop is secured alongside the suture strand outside the accessory portal.
Figure 11:
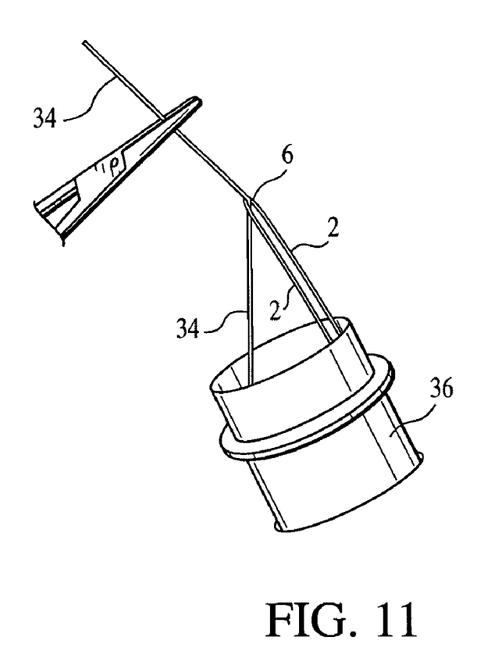
FIG. 11 illustrates a step subsequent to the step shown in FIG. 10, in which the end of the suture strand is passed through the radius of the nitinol loop.
Figure 12:
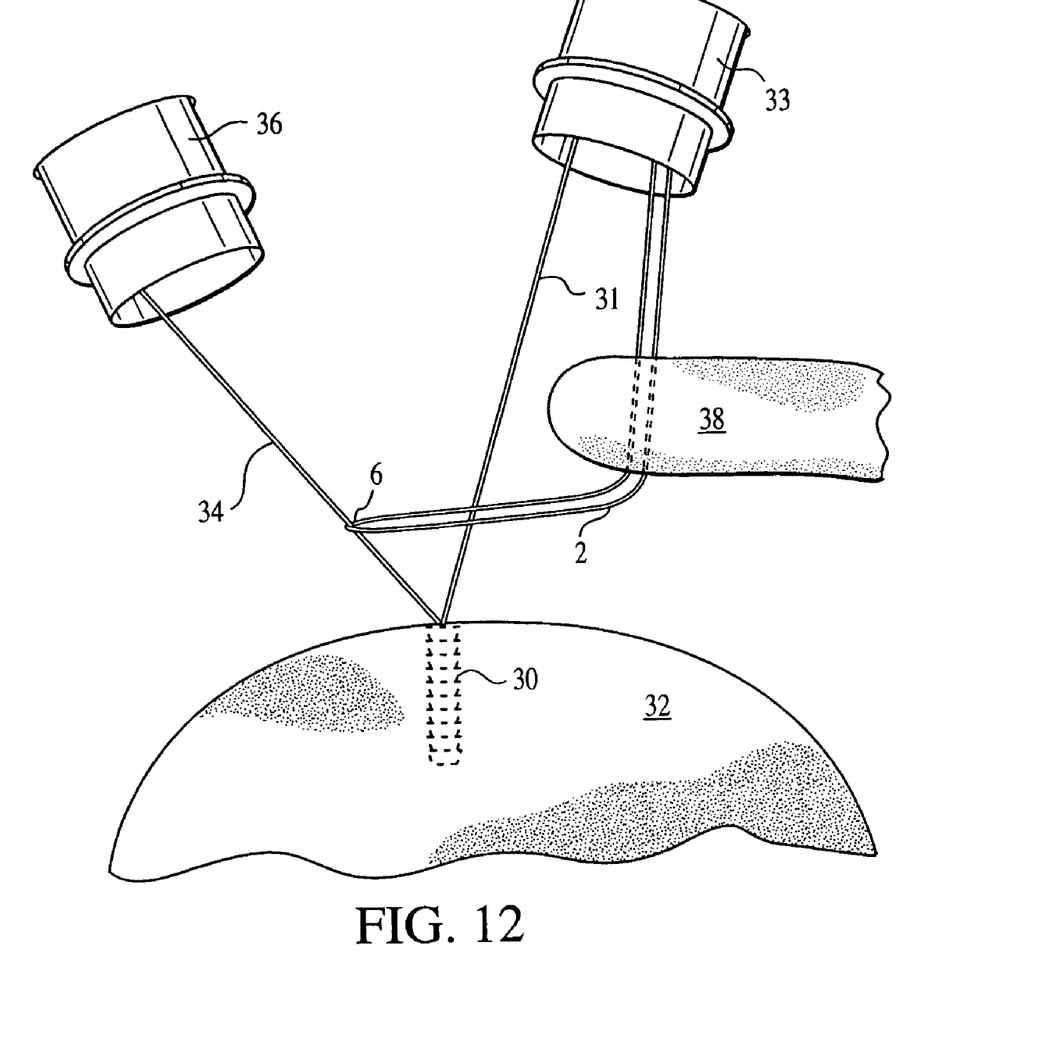
FIG. 12 illustrates a step subsequent to the step shown in FIG. 11, in which the nitinol loop is retracted back into the body through the accessory portal, carrying the suture strand.

Referring now to FIG. 10, nitinol loop 2 is secured alongside suture strand 34 outside accessory portal 26. While holding nitinol loop 2 with either an instrument (as shown in FIG. 10) or with a finger, passer 20 is retracted through portal 33, leaving nitinol loop 2 extending from portal 33 though capsule tissue 38 and extending out through accessory portal 26. As shown in FIG. 11, end of suture strand 34 is then passed through the radius 6 of nitinol loop 2. Next, nitinol loop 2 is retracted back through accessory portal 36, with radius 6 carrying secured suture strand 34, as shown in FIG. 12.

Figure 13:
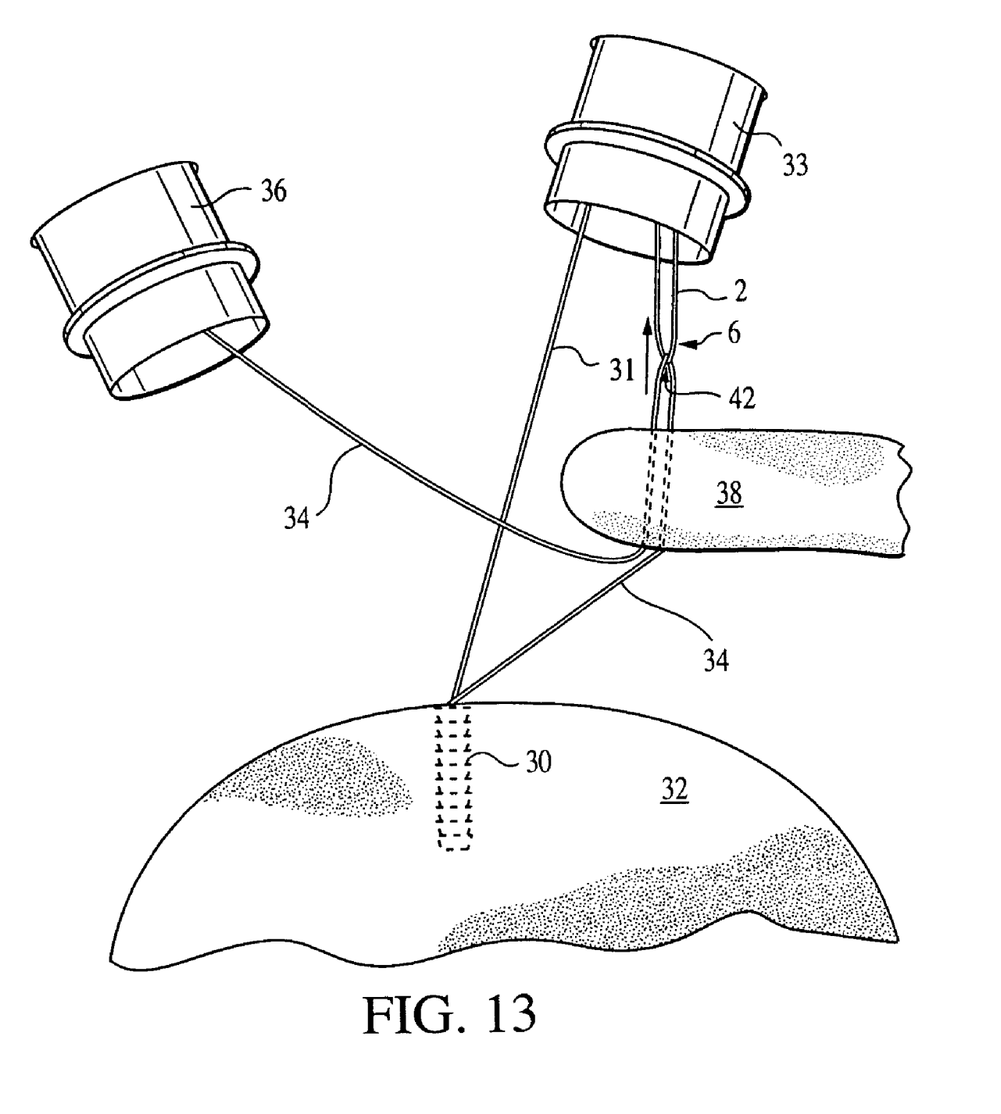
FIG. 13 illustrates a step subsequent to the step shown in FIG. 12, in which the nitinol loop is further retracted so that it passes through the tissue to be sutured.
Figure 14:
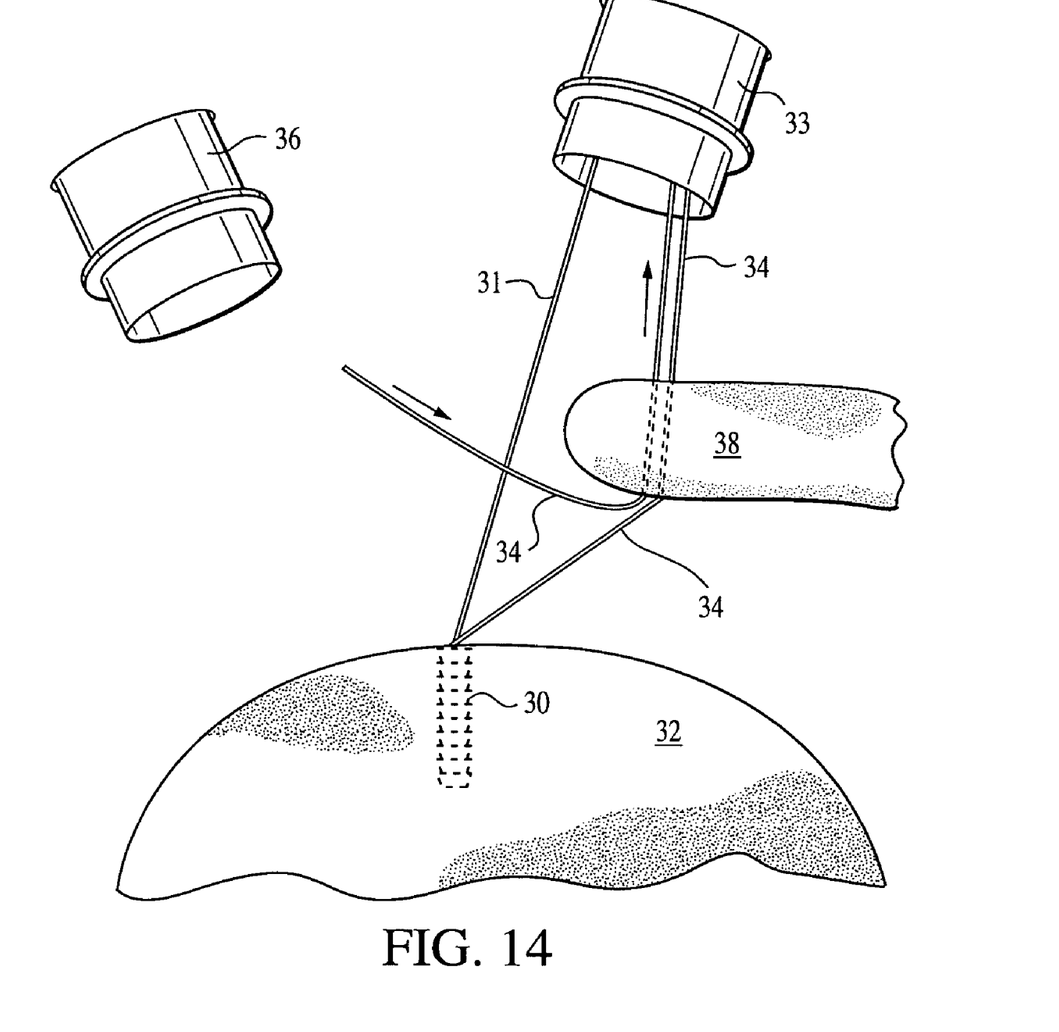
FIGS. 14–16 illustrates steps subsequent to the step shown in FIG. 13, in which the nitinol loop is retracted from the portal, pulling the suture strand through the tissue to be sutured and out through the portal.
Figure 15:
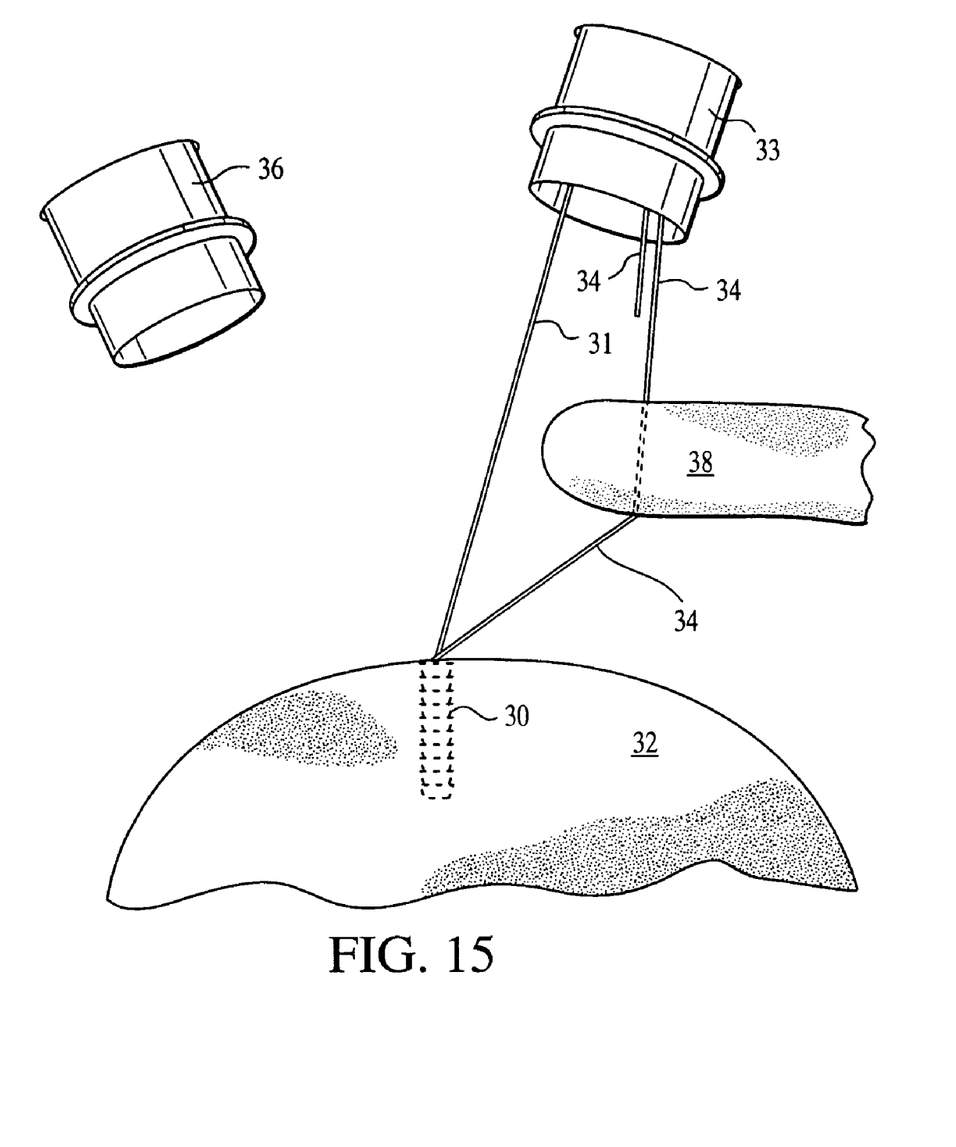
Figure 16:
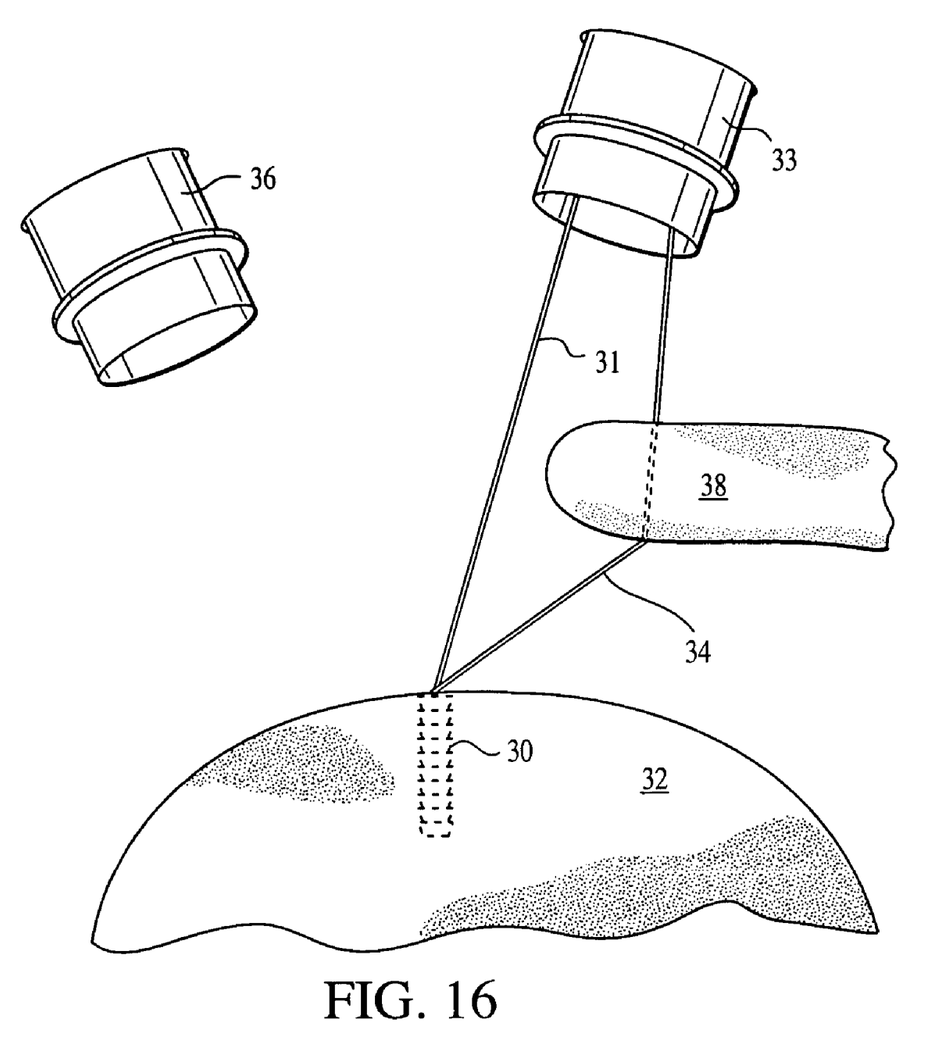

Referring next to FIG. 13, nitinol loop 2 is further retracted so that it passes through capsule tissue 38. End of suture strand 34 is released or provided slack on the exterior end of accessory portal 36 to allow suture strand 34 to form a flexible radius 42 about radius 6 of nitinol loop 2. Nitinol loop 2 is then retracted from through portal 33, pulling suture strand 34 through capsule tissue 38 and out through portal 33, as shown in FIGS. 14–16.

Figure 17:
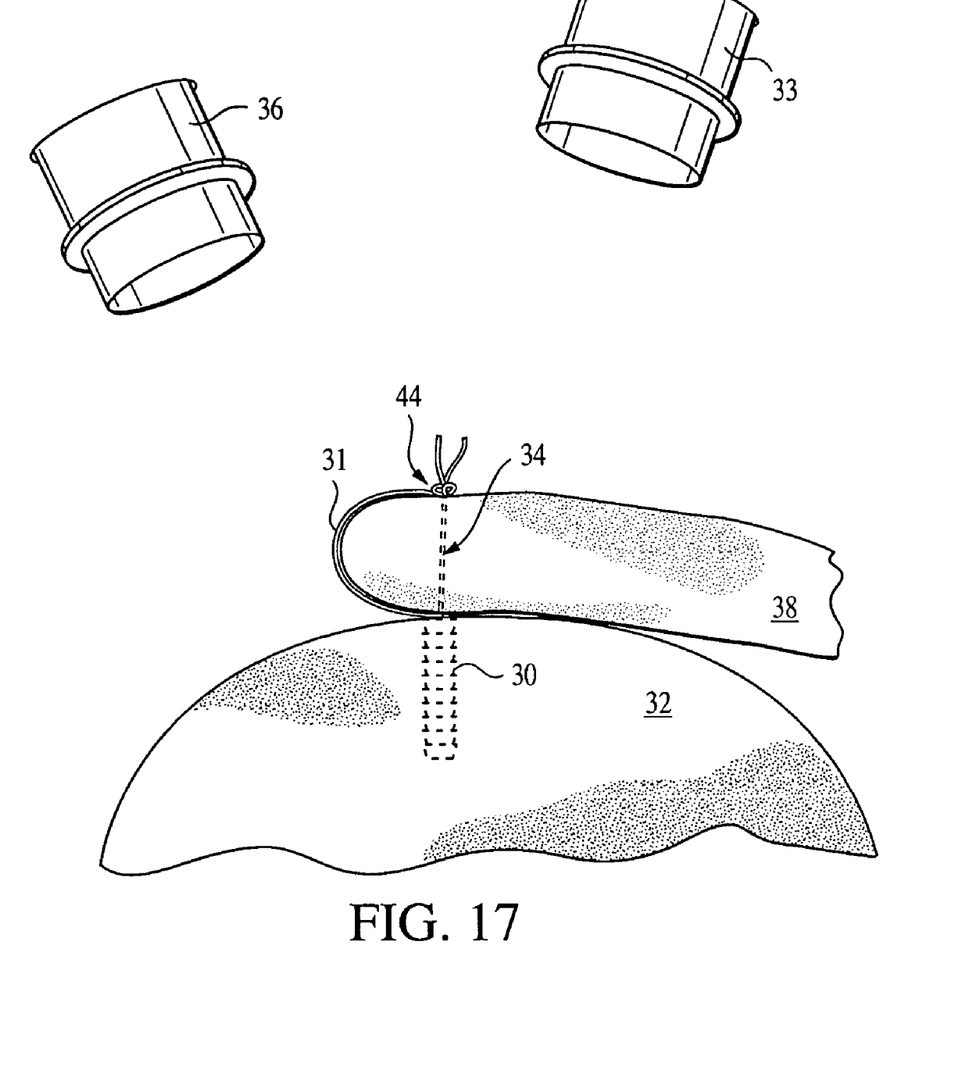
FIG. 17 illustrates the final step in which the tissue is secured against the bone by an arthroscopic knot tied between the two suture strands.

At this point, arthroscopic knots between suture strand 34 and suture strand 31 are tied and advanced in the normal fashion using, for example, an Arthrex CrabClaw Knot Pusher, disclosed in pending application Ser. No. 10/357, 449, to secure capsule tissue 38 against bone 32, as shown in FIG. 17.

The above description and drawings are only to be considered illustrative of exemplary embodiments which achieve the features and advantages of the invention. Although exemplary embodiments of the present invention have been described and illustrated herein, many modifications, even substitutions of materials, can be made without departing from the spirit or scope of the invention. For example, although the present invention is described as a technique for fixing a lax shoulder capsule to a bone, it should be apparent that the technique of the present invention is appropriate for fixing other kinds of tissue. Accordingly, the above description and accompanying drawings are only illustrative of exemplary embodiments that can achieve the features and advantages of the present invention. It is not intended that the invention be limited to the embodiments shown and described in detail herein. The invention is limited only by the scope of the appended claims.

What is claimed as new and desired to be protected by Letters Patent of the United States is:

1. A method of securing tissue to bone, comprising the steps of:
   installing a suture anchor with an attached suture strand in a portion of bone adjacent a section of tissue to be secured;
   piercing said tissue with a sharp distal end of a cannulated suture passing instrument;
   passing a strand of flexible metallic material, formed into an elongated loop having a crimped end with an acute bend, through the cannulated suture passing instrument;
   deploying said loop formed of flexible metallic material from the sharp distal end of said carinulated suture passing instrument;

capturing said suture strand with said loop; and passing said captured suture strand through said tissue by retracting the loop through the tissue.

2. The method of claim 1, further comprising the steps of:

retrieving and passing said suture strand through an accessory portal;

retrieving and passing said loop through the accessory portal; and capturing said suture strand with said loop outside of the accessory portal.

3. The method of claim 1, wherein said suture stand is captured in said loop by threading said suture strand through a radius of said loop.

4. The method of claim 2, further comprising the step of retracting said suture passing instrument through said portal, leaving said flexible loop passing through said tissue.

5. The method of claim 1, further comprising the step of forming a knot between said suture strand and a second suture stand also attached to said suture anchor.

* * * * *